(12) United States Patent
Kreindel et al.

(10) Patent No.: US 6,387,089 B1
(45) Date of Patent: *May 14, 2002

(54) METHOD AND APPARATUS FOR SKIN REJUVINATION AND WRINKLE SMOOTHING

(75) Inventors: Michael Kreindel; Shimon Eckhouse, both of Haifa (IL)

(73) Assignee: Lumenis Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/307,874

(22) Filed: May 10, 1999

Related U.S. Application Data

(63) Continuation-in-part of application No. 08/529,044, filed on Sep. 15, 1995, now Pat. No. 5,964,749.

(51) Int. Cl.[7] ................................. A61N 5/06
(52) U.S. Cl. ............................. 606/9; 607/88
(58) Field of Search ....................... 606/2, 3, 8, 9, 606/10; 607/88, 89, 90, 91

(56) References Cited

U.S. PATENT DOCUMENTS

| | | |
|---|---|---|
| 2,699,771 A | 1/1955 | Ruttger-Pelli |
| 4,022,534 A | 5/1977 | Kishner |
| 4,298,005 A | 11/1981 | Mutzhas |
| 4,608,978 A | 9/1986 | Rohr |
| 4,686,986 A | 8/1987 | Fenyo et al. |
| 4,757,431 A | 7/1988 | Cross et al. |
| 4,784,135 A | 11/1988 | Blum et al. |
| 4,829,262 A | 5/1989 | Furumoto |
| 4,930,504 A | 6/1990 | Diamantopoulos et al. |
| 4,950,880 A | 8/1990 | Hayner |
| 4,976,709 A | 12/1990 | Sand |
| 5,139,494 A | 8/1992 | Freiberg |
| 5,161,526 A | 11/1992 | Hellwing et al. |
| 5,207,671 A | 5/1993 | Franken et al. |
| 5,217,455 A | 6/1993 | Tan |
| 5,226,907 A | 7/1993 | Tankovich |
| 5,259,380 A | 11/1993 | Mendes et al. |
| 5,282,797 A | 2/1994 | Chess |
| 5,320,618 A | 6/1994 | Gustaffson |
| 5,336,217 A | 8/1994 | Buys et al. |
| 5,344,418 A | 9/1994 | Ghaffari |
| 5,344,434 A | 9/1994 | Talmore |
| 5,374,265 A | 12/1994 | Sand |
| 5,409,479 A | 4/1995 | Dew et al. |
| 5,527,350 A | 6/1996 | Groove et al. |
| 5,591,157 A | 1/1997 | Hennings et al. |
| 5,611,795 A | 3/1997 | Slatkine et al. |
| 5,660,836 A | 8/1997 | Knowlton |
| 5,769,844 A | * 6/1998 | Ghaffari .................... 606/2 |
| 5,964,749 A | * 10/1999 | Eckhouse et al. ............ 606/9 |

FOREIGN PATENT DOCUMENTS

| | | |
|---|---|---|
| DE | 3906860 A1 | 3/1989 |
| EP | 0565331 A2 | 10/1993 |

OTHER PUBLICATIONS

Diffusion of Light in Turbid Material, A. Ishimaru, Applied Optics 1989, vol. 28, No. 12, pp. 2210–2215.
Improved Efficacy of SnET2 Mediated PDT With the Simultaneous Application of Selective Laser–Indused Hyperthermia, A. C. Lytle, D. D. Severson, D. R. Doiron, A. Ferrario, C. J. Gomer, SPIE Proceedings, vol. 2392–06.
R. R. Anderson, J.A. Parish, in Surg. Med., vol. 1, p. 263, 1981.
J. Morreli, O. T. Tan, et al., in Lasers Surg. Med., vol. 6, No. 1, p. 94, 1986.
L. L. Pola, O. T. Tan. J. M. Garden, et al., in Drematologica, vol. 174, p. 11, 1987.
Role of Skin Optics in Diagnostic and Therapeutic Uses of Lasers, S. L. Jacques, Springer–Verlag, 1991, pp. 1–21.
Whole–Body Hyperthermia in Cancer Therapy: A Report of A Phase I–II Study, J. van der Zee, et al., Eur. J., Cancer Clinical Oncology, 1983, vol. 19, No. 9, pp. 1189–1200.
Relationship of Response to Transurethral Hyperthermia and Prostate Volume in BPH Patients, Z. Patrovich, F. Ameye, M. Pike, S. Boyd, L. Baert, Urology, 1992, vol. 40, No. 4, pp. 317–321.
YAG Laser–Induced Hyperthermia in a Mouse Tumor Model, S.M. Waldow, P.R. Morrison, C.I. Grossweiner, Lasers in Surgery and Medicine, 1988, vol. 8, No. 5 pp. 510–514.
Light & Electron Microscopic Analysis of Tattoos Treated by O–Switched Ruby Laser, C. Taylor, R.R. Anderson, et al., J. of Investigative Dermatology 1991, vol. 97, pp. 131–136.
Treatment of Benign Cutaneous Pigmented Lesions with the Candela 510 NM Pulsed Laser, Laser Med. and Surgery Abstracts, R.E. Fitzpatrick et al., 1992, vol. 4s, p. 73.
Treatment of Pigmented Lesions with the Flashlamp Pumped PL DL ("Brown Spot") Laser, Laser Med. And Surgery Abstracts, G.J. Brauner, M.D. et al., 1992, vol. 4s., p. 73.

* cited by examiner

Primary Examiner—Eric F. Winakur
(74) Attorney, Agent, or Firm—Eitan, Pearl, Latzer & Cohen-Zedek

(57) ABSTRACT

A method and apparatus for treating skin including applying pulsed light to the skin for heating and shrinking collagen within the skin, thereby reviving the elasticity of the collagen and of the skin. The epidermis and outer layers of the skin may be protected by cooling with a transparent substance, such as ice, gel or crystal.

The temperature distribution within the skin is controlled by controlling the delay between the time the coolant is applied, and the time the light is applied, by controlling the pulse duration and applying multiple pulses, and by filtering the light and controlling the radiation spectrum. Preferably, the spectrum includes light having a wavelength in the range of 500–2000 nm. The pulsed light may be incoherent, such as that produced by a flashlamp, or coherent, such as that produced by a Nd(Yag) laser, an Alexandrite laser, a Diode laser, an Er:glass laser or a ruby laser, and may be directed to the skin using a flexible or rigid light guide.

9 Claims, 4 Drawing Sheets

METHOD AND APPARATUS FOR SKIN REJUVINATION AND WRINKLE SMOOTHING

REFERENCE TO RELATED APPLICATIONS

This application is a continuation-in-part application of U.S. patent application Ser. No. 08/529,044, filed Sep. 15, 1995, now U.S. Pat. No. 5,964,749.

FIELD OF THE INVENTION

The present invention relates generally to the art of skin treatment using electromagnetic radiation. More particularly, the invention relates to an efficient method and apparatus for skin rejuvenation by ablation of the outer layer of the skin and wrinkle smoothing (or shrinking) by heating of collagen without damage to the epidermis.

BACKGROUND OF THE INVENTION

There is a strong desire today to obtain and/or maintain a youthful appearance. One manner of doing so is to remove (or reduce) wrinkles. Additionally, it is desirable to rejuvenate the skin by removing an outer layer of skin. There are known techniques for removing wrinkles by peeling the skin. Also, there are known methods for rejuvenating the skin. Unfortunately, all known techniques suffer from lack of efficacy and risk to the patient.

One known method of skin rejuvenation includes injection of collagen underneath the skin. This has been performed using a bovine collagen injection. For example, microfine collagen has been injected into periocular lines. Some of the problems with collagen injection include allergy to collagen and lack of longevity. Also, often there is only partial eradication of the wrinkles.

Peeling most or all of the outer layer of the skin is another known method of rejuvenating the skin. Peeling can be achieved chemically, mechanically or photothermally. Chemical peeling is often carried out using trichloroacetic acid and phenol. An inability to control the depth of the peeling, possible pigmentary change and risk of scarring are among the problems associated with chemical peeling.

The mechanical method is called transcutaneous blepharoplasty and involves shaving off the outer layer of skin. Skin resection during lower lid blepharoplasty frequently results in undesirable side effects, especially ectropion and scleral show. Moreover, transcutaneous blepharoplasty rarely eradicates all of the wrinkle lines.

Pulsed carbon dioxide laser treatment is a known photothermal method of removing of periocular wrinkles. However, laser light is heavily absorbed in water and has a very short range in the epidermis. Thus, a high fluence with short pulse durations will evaporate the outer layer of the skin and peels most or all of the epidermis and simultaneously heat deeper skin layers that cause collagen shrinkage.

The use of $CO_2$ laser light for skin rejuvenation also has undesirable side effects. For example, $CO_2$ lasers have small spot size (3 mm or less), and thus their use causes valleys and ridges, particularly when resurfacing large areas. Also, it is difficult to control heat diffusion, and thus the resultant necrosis is difficult to predict and control. Additionally, scar tissue absorbs $CO_2$ laser light differently than normal skin and thus may adversely impact such a treatment.

Another known method of skin peeling uses an Er:Yag laser. The small penetration depth of the Er:Yag laser enables removing of the outer layer of the skin without causing collagen heating. A treatment of that kind helps the skin to look younger, but does not help to smooth deep wrinkles.

Thus, it is apparent there is a need for a new method and device with which it is possible to produce efficient wrinkle removal and skin rejuvenation. This apparatus would preferably be able to control the treatment parameters according to characteristics of the tissue, and be easily tunable. The new method and device would preferably provide efficient wrinkle smoothing and skin rejuvenation without removing outer skin layers and with minimal side effects.

SUMMARY OF THE PRESENT INVENTION

In accordance with one aspect of the invention there is provided a method and apparatus for treating skin including applying pulsed light to the skin for heating and shrinking collagen within the skin, thereby reviving the elasticity of the collagen and of the skin. In one embodiment the method also includes protecting the epidermis and outer layers of the skin by cooling the epidermis and outer layers of the skin. The cooling may be accomplished by applying a cooled transparent substance, such as ice, gel or crystal, to the skin.

In one alternative embodiment the skin is cooled by first applying the transparent substance to the skin and then cooling it.

In another alternative embodiment the temperature distribution within the skin is controlled by controlling the delay between the time the coolant is applied, and the time the light is applied. A microprocessor may be used for determining the delay time in response to a selected skin temperature profile. Additionally, the temperature distribution may be controlled by controlling the pulse duration and applying multiple pulses. In another embodiment the temperature distribution within the skin is controlled by filtering the light and controlling the radiation spectrum. Preferably, the spectrum includes light having a wavelength in the range of 600–1600 nm.

In another embodiment the pulsed light may be incoherent, such as that produced by a flashlamp, or coherent, such as that produced by an Nd(Yag) laser, an Alexandrite laser, a Diode laser, an Er:glass laser or a ruby laser.

In another embodiment the light is directed to the skin using a flexible or rigid light guide.

In accordance with a second aspect of the invention there is provided a method and apparatus for generating a temperature distribution inside a region of skin having a maximum temperature at a selected depth including cooling the epidermis and outer layers of the skin and applying pulsed light to the skin.

In one embodiment the cooling is accomplished by applying a cooled transparent substance, such as gel, ice or crystal, to the skin. Alternatively, the cooling may be accomplished by first applying the transparent substance, and then cooling it.

The temperature distribution is further controlled in one embodiment by controlling the delay between the cooling and the light application. In another embodiment the distribution is controlled by controlling the pulse duration and/or applying multiple pulses.

Other principal features and advantages of the invention will become apparent to those skilled in the art upon review of the following drawings, the detailed description and the appended claims.

Figure 1:
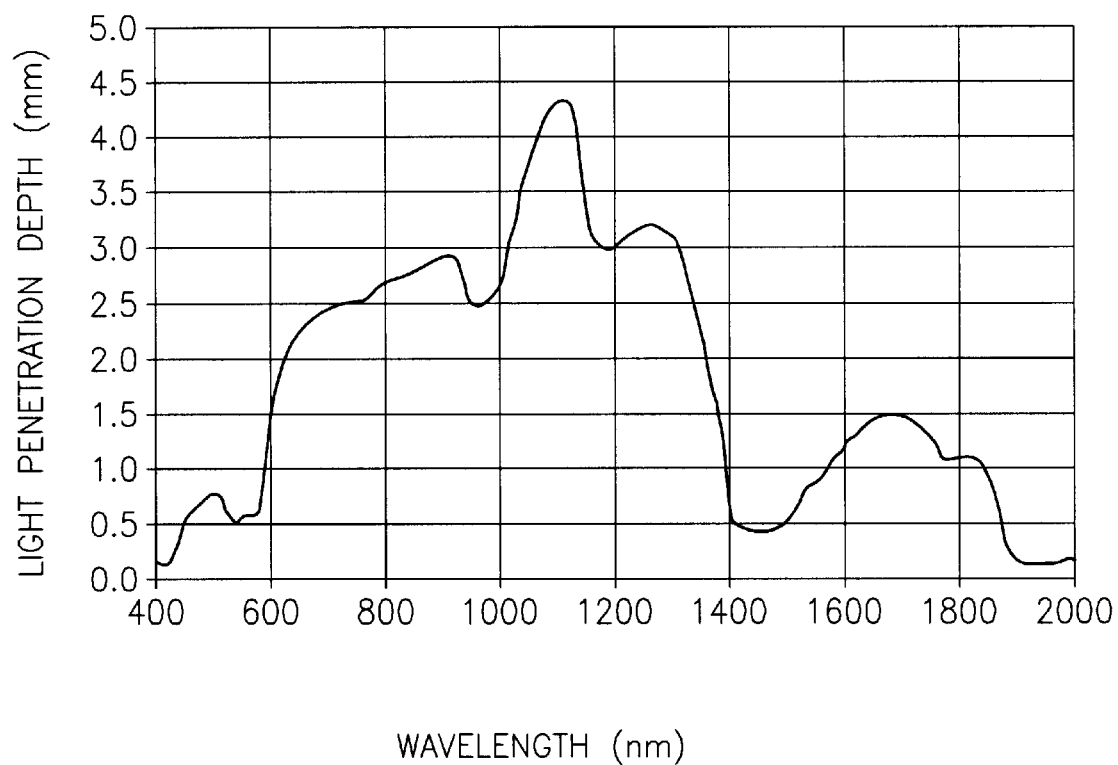
FIG. 1 shows the light penetration depth into the tissue as function of the wavelength of the light source.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

The invention relates to a new method and apparatus for removing wrinkles and rejuvenating skin. Generally, in accordance with this invention, wrinkles are smoothed or reduced by collagen shrinking and increasing the elasticity of the skin and collagen, using a short heating impulse. Tissue is heated at a depth of up to a few millimeters by light radiation, while the skin is externally cooled at the surface to avoid overheating the epidermis. The epidermis may be cooled in a variety of ways, including applying a precooled (i.e., a temperature less than the ambient temperature) transparent substance such as ice, cold gel or cold crystal to the skin. The cold substance should cool the skin before and during treatment. The light (electromagnetic radiation) is applied to the skin in pulses shortly after the application of the cooling material. Alternatively, the ice, gel or crystal could be applied to the skin or skin surface, and then cooled (using thermoelectric cooler, e.g.) shortly before the application of the pulsed light to the skin.

The light source will preferably provide a spectrum such that the optical depth of penetration into the tissue is of the order of 1 mm or more. Also, the light source will preferably be able to provide pulses having fluences of the order of 5–60 J/cm$^2$ and peak power of the order of 100–10,000 W/cm$^2$. A spot size of the order of 10 mm is preferable, to reduce scattering losses.

Laser light sources that should be appropriate include a Nd(Yag) laser, a ruby laser, an Alexandrite laser, an Er:glass laser, diode lasers and other suitable lasers. Incoherent light sources such as a xenon flashlamp should also be appropriate.

A method for cutaneous resurfacing (skin rejuvenation) in accordance with the present invention includes use of an ER:YAG laser light, which has a most efficient wavelength of 2.94 μm. Because the absorption depth of an ER:YAG laser in skin is very small (less than 20 microns), it may be difficult to ablate to a depth of the order of 100 microns or more (typical of the epidermis) with it. However, a deeper depth of peeling can be achieved by extending the pulse length of the laser. While this is hard to achieve using an ER:YAG laser due to the inherent short level lifetime, by providing a few pulses with a variable delay between the pulses this limitation may be overcome. Evaporated tissue layer thickness may be controlled by the number of pulses and variation of pulse parameters and delay between pulses.

The invention also relates to an apparatus using a flashlamp light source, or any other source with appropriate parameters, for smoothing wrinkles, without damaging the epidermis. Also, an ER:YAG laser is used for efficient skin rejuvenation by removal of the epidermis.

Generally, the device includes a flashlamp that can provide a pulsed light in the range of 500–2000 nm for heating of collagen, a filter system that can cut off the radiation is spectrum below approximately 600 nm, a light guide that can provide an appropriate spot size and can provide fluences of the order of 5–200 J/cm$^2$, and an ER:YAG laser with pulse energy of the order of 1 J, which can be operated in multiple pulse mode with delays between pulses of less than 50 msec for skin rejuvenation (by skin ablative peeling).

In one alternative, a light source such as an Nd(Yag) laser, an Alexandrite laser, a Diode laser, an Er:glass laser or ruby laser with appropriate parameters, could replace the flashlamp.

This apparatus is very useful for wrinkle removal and skin rejuvenation. A flashlamp light source, particularly when used with external cooling of skin surface, will generate a temperature distribution inside the skin which has a maximum at depth dependent on the light and cooling. Consequently, it is possible to heat collagen molecules without damaging the epidermis. The temperature distribution in the skin is responsive to the delay time between the cooling and application of light, selection of pulse parameters and the radiation spectrum. Accordingly, appropriate control of these parameters allows control of the temperature distribution. An ER:YAG laser operated in multiple pulse mode is very efficient for cutaneous resurfacing procedures and also enables control of depth of evaporation. Thus, the apparatus is safe with little risk of accidental injury to the operator and patient.

As stated above, wrinkles may be smoothed by shrinking collagen using pulsed heating. The method of the present invention is realized by heating of tissue to depths of up to a few millimeters by light radiation in association with external cooling of the outer surface of the skin to avoid overheating of epidermis.

The thickness of the heated collagen influences the efficiency of the treatment. In order to perform a successful treatment, light should penetrate through the epidermis (the superficial layer of skin) and be absorbed in the dermis. Typical epidermis thickness is in the range of 50–100 microns. Typical dermis thickness is in the range of 0.5 to 3 mm. Consequently, in order to heat collagen without overheating the epidermis, the light penetration depth into the skin should be larger than 100 microns, and can be varied in the range of 0.5 to 3 mm. Light penetration depth as function of wavelength of the light source is presented in FIG. 1. As can be seen in FIG. 1, wavelength in the range of 500 to 1900 nm is appropriate in order to achieve deep collagen heating. Preferably, the wavelength is in the range of 600 to 1600 nm.

Figure 2:
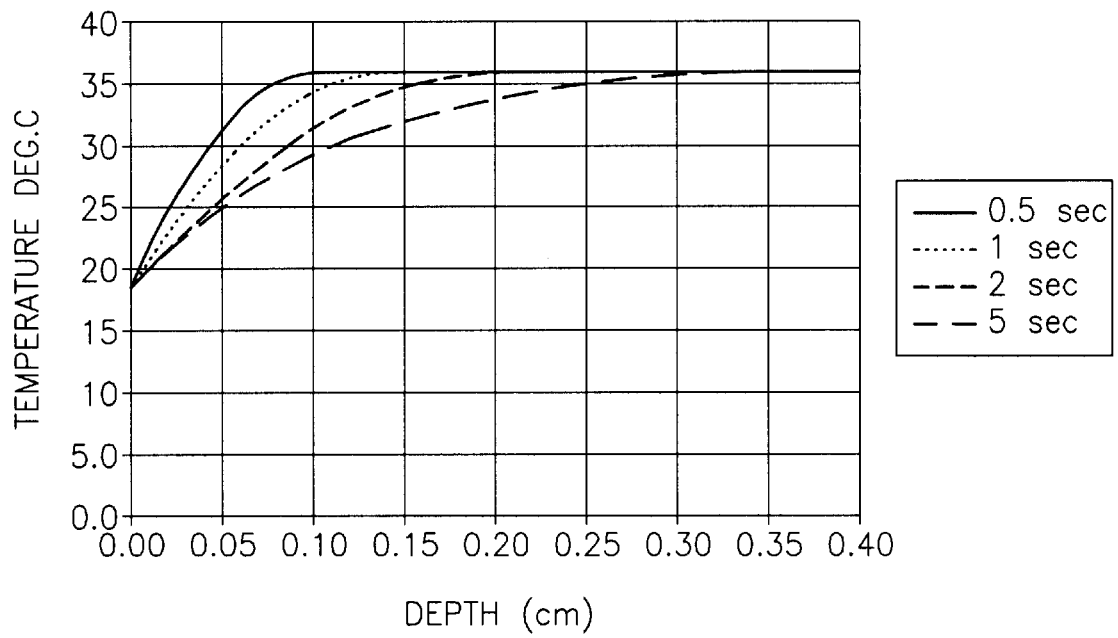
FIG. 2 shows a temperature distribution achieved inside the skin after a cold fluid was applied to the skin, for a plurality of different time delays after the application of the cold gel.

The epidermis may be cooled using many methods. One preferred method is the application of a previously cooled transparent matter like ice, cold gel or cold crystal on the skin which cools the skin before and during treatment. A temperature distribution inside the skin similar to the one shown in FIG. 2 is created a short time (of the order of 1 second) after the application of the cooled material.

As may be seen, the distribution is such that the epidermis and the outer layer of the skin are colder than the more deeper part of the skin. However, the applied light heats up the superficial parts of the skin more than the inner parts, because of the attenuation of light energy fluence by depth, and due to higher absorption of light by the epidermis.

Figure 3:
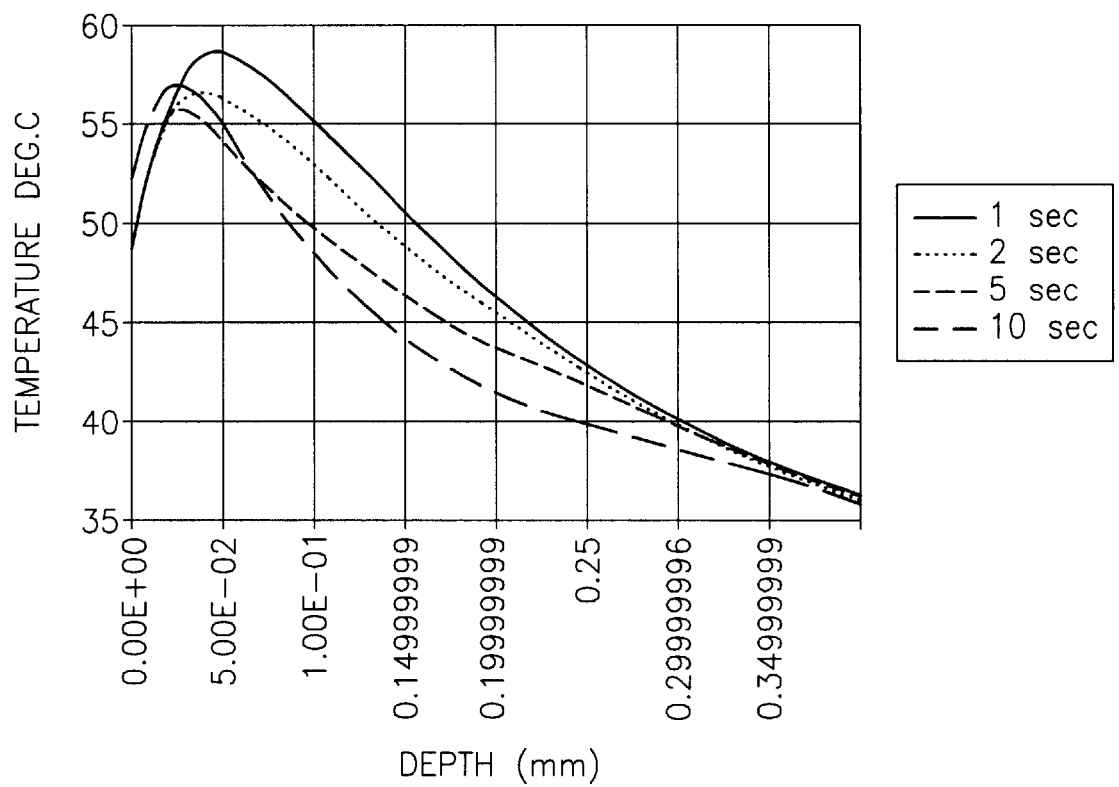
FIG. 3 shows a temperature distribution achieved by precooling the skin and applying the light source.

After heating, a temperature distribution such as that shown in FIG. 3 results. As may be seen, the deeper parts of the tissue are heated up to a temperature sufficient to cause collagen shrinking, but without damaging the outer parts of the skin (epidermis).

The temperature distribution generated prior to the application of light (FIG. 2) is a function of the initial temperature of the cooling material and the delay time between the application of the cooling material and the application of light. By varying this time the depth of penetration of the "cool front" can be varied. When collagen that is deeper needs to be treated without influencing the superficial skin, a longer delay time between the application of the coolant and the light can be used. When the superficial collagen needs to be treated, a shorter delay time can be used.

In a typical treatment the doctor applies the cold gel to the skin before treatment and then applies the light source. In accordance with one embodiment of the invention, the treatment device indicates to the doctor when the light source needs to be applied after application of the cooling material, to achieve a desired temperature distribution. A microprocessor that controls the light generating device may also generate a timing signal for the doctor to accomplish this aspect of the invention.

The applicants have determined that a light source having the following parameters is suitable for implementing the invention:

Light radiation should penetrate into a tissue at a millimeter depth. Examples of light sources which meet the parameter include flashlamp, diode laser, Nd(Yag) laser, Alexandrite laser, Er:glass laser and ruby laser. Optical power may be on the order of 100–10,000 W/cm$^2$. Fluence may be on the order of 5–200 J/cm$^2$. Wavelength range can be from 500 nm (or 600 for a laser) to 2000 nm.

Spot size should be on the order of a few millimeters to some centimeters, preferably variable over a range. The spot size can vary from 1 mm to 10 cm.

Figure 4:
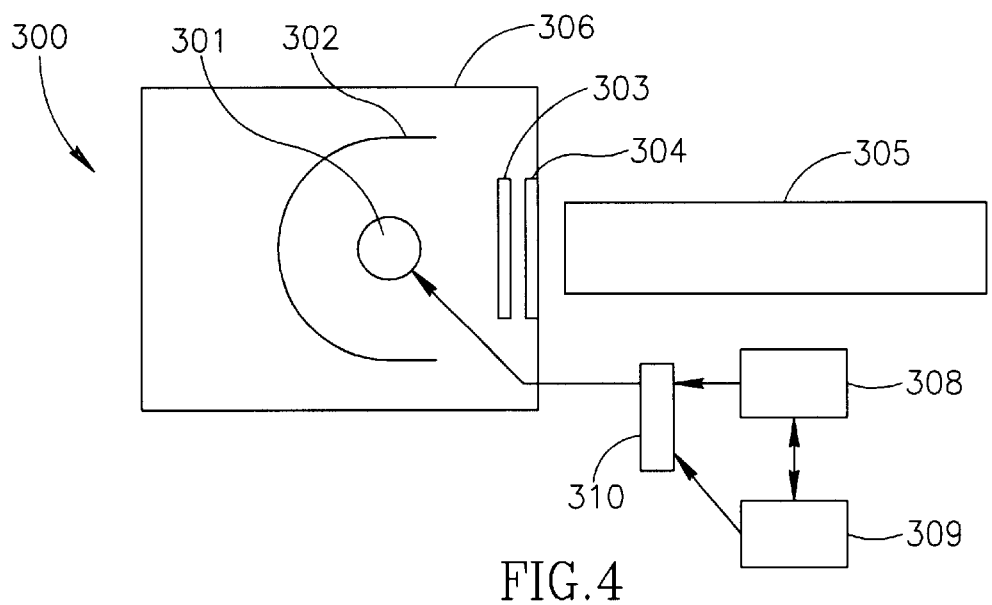
FIG. 4 is a schematic illustration of the flashlamp light source according to one preferred embodiment of the present invention.
Figure 5:
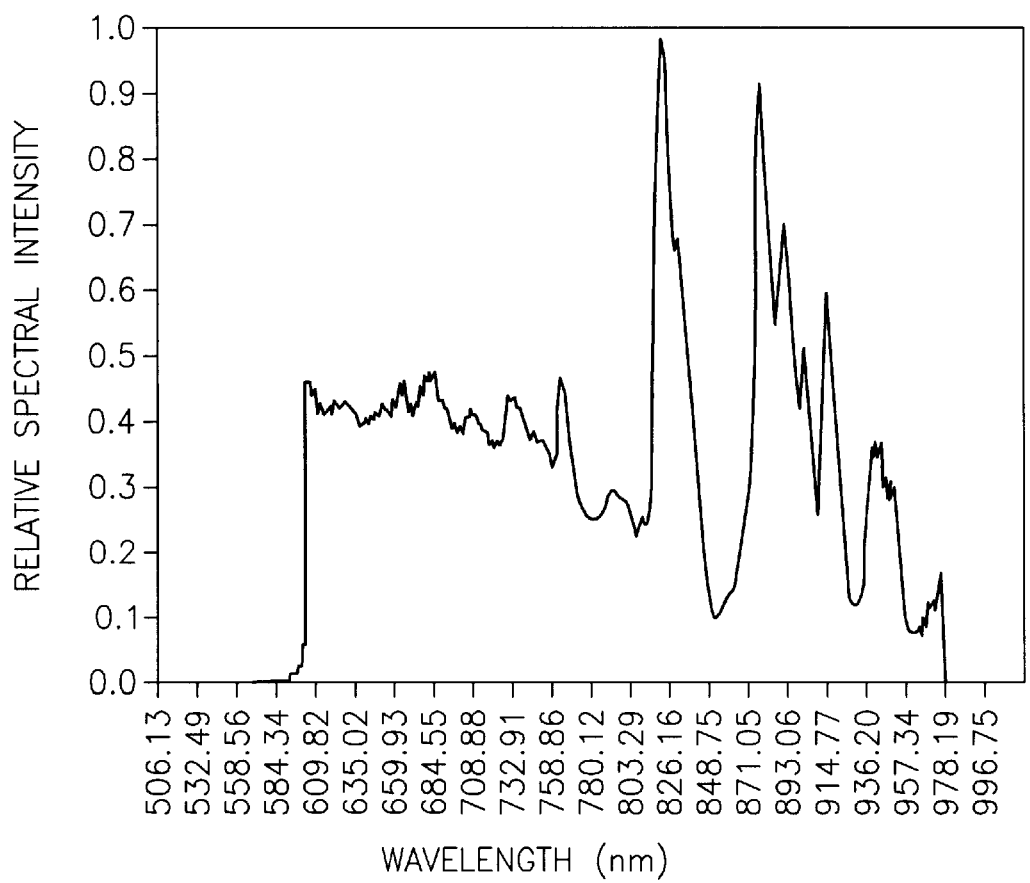
FIG. 5 shows a normalized output filtered radiation spectrum of a flashlamp light source.

A detailed description of one preferred embodiment will be described with reference to FIG. 4. As shown in FIG. 4, a treatment device 300 includes a flashlamp 301 which can be operated in pulse mode, a reflector 302 which forms a light beam and conducts it to a light guide 305 through a filter system 303 and 304. Reflector 302 is located in a treatment head (or housing) 306.

Filter system 303 and 304 may include one or more filters which cut off the radiation spectrum at approximately 550(or 600)–800 nm. Filter 303 provides reflection of the part of unused incident radiation and avoids overheating of absorbing filter 304. The absorbing filter cuts off radiation at approximately 550–800 nm. Flexible light guide 305 can be interchanged with a rigid light guide made out of quartz or other types of high optical quality glass. Treatment head 305 is useful for treating large areas.

According to one embodiment, the light energy is applied to the skin using a train of pulses. A long pulse may be required for the treatment of the skin, such a pulse may be modulated from shorter pulses with short delays. One advantage of applying a long pulse or a train of short pulses is that the epidermis is cooled down faster relative to the layer of collagen that is heated in the treatment. Preferably, the apparatus produces a train of pulses with variable delays between pulses in the range of 1 to 100's of milliseconds. Pulse duration can be in the range of 1 to 300 milliseconds. Preferably, pulse duration is in the range of 10–100 milliseconds. Repetition rate can be from 0.1 to 1000 pulses per second. Preferably, the repetition rate is 0.1–20 pulses per second.

The total number of pulses per pulse train can also be varied. More specifically, for a patient with higher skin absorption due to heavier skin pigmentation a larger number of pulses per train is preferably used.

Similarly, the pulse duration of each pulse in the train can also be varied in order to enable cooling of the epidermis without cooling the collagen. In any event, the total dose to the treated area is the product of the number of pulses and the fluence per pulse. The pulse duration and train length are controlled in one embodiment by a microprocessor 309. As shown on FIG. 4, microprocessor 309 provides control signals to pulse forming network 310. Pulse forming network 310 (generally of the type described in commonly owned U.S. Pat. No. 5,405,368, which is incorporated herein by reference) provides pulse to flashlamp 301.

The radiation spectrum can be controlled by filter system 303 and 304. Additionally (or alternatively), the spectrum of radiation can be controlled by varying the current density through the flashlamp. If deeper heating is requiredm a longer wavelength radiation is used.

Other embodiments of the present invention include the use of lasers (those having proper penetration), which can also be very effective to smooth wrinkles. For example, a flashlamp pumped Nd(Yag) laser operating at 1.06 $\mu$m can provide deep penetration and thus be effective. The laser may be operated in the pulsed train mode, preferably by pulsing the flashlamps that are used to pump the laser. Similarly, a ruby laser may be used, an Alexandrite laser, a Diode laser, or an Er:glass laser. However, the pulse duration cannot be made too long due to the limited value of the lifetime of the lasing level of these lasers. In the laser embodiment, there is no need for filters since the light is monochromatic. Also, this embodiment does not require the use of a rigid light guide since flexible light guides are readily available for laser applications and a low divergence laser beam can be easily focused into a small diameter optical fiber. The use of multiple pulses may be particularly useful to overcome the limited lasing level in the laser embodiment of the invention.

Another embodiment of the present invention may include employing a laser scanner. U.S. Pat. No. 5,611,795, dated Mar. 18, 1997, belonging to the same assignees of this patent application, describes using a scanner in combination with a CO$_2$ laser.

Figure 6:
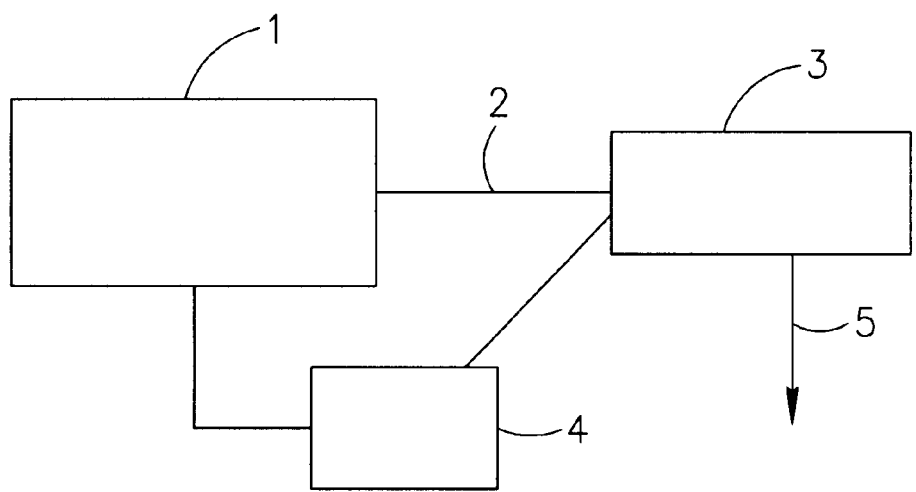
FIG. 6 is a schematic illustration of a laser light source employing a laser scanner.

A laser scanner is an element used for achieving a uniform covering of a surface by laser radiation. FIG. 6 is a schematic illustration of a laser light source employing a laser scanner. A laser 1 produces radiation that is delivered to a scanner 3 through delivery system 2. The operation of scanner 3 is synchronized with the operation of laser 1, by a scanner controller 4. The output laser beam 5 is directed to cover the skin surface, thus providing uniform skin resurfacing.

Figure 7:
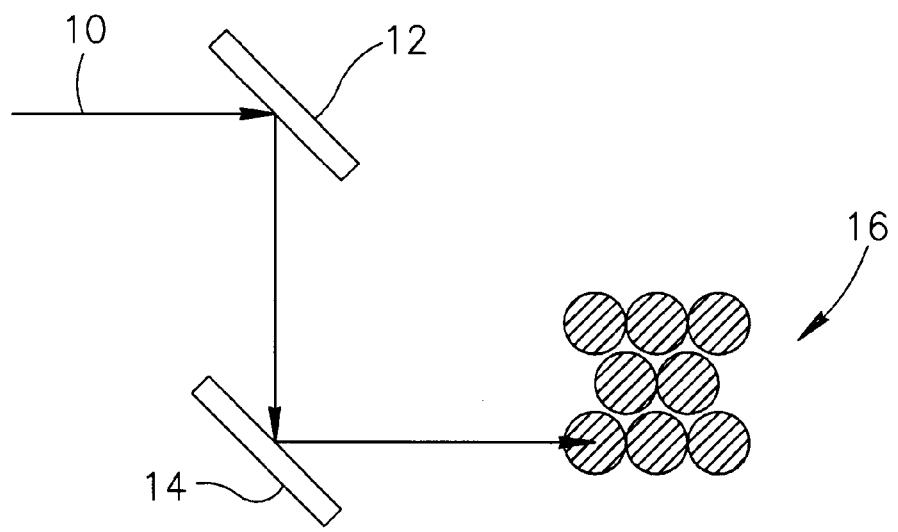
FIG. 7 is a schematic illustration of a laser beam trajectory through the laser scanner preferably used in the present invention.

Reference is now made to FIG. 7, which schematically shows the laser beam trajectory through a scanner preferably used in the present invention. The laser scanner of the present invention consists of two rotated mirrors 12 and 14 which change the direction of the laser beam 10, in order to achieve a desired spot arrangement 16 on the skin, and thus to cover the skin optimally. Additionally, as a result of using a laser scanner, lasing in a high repetition rate is possible, as pulses can be directed to the treated region of skin in advance, instead of addressing each pulse individually.

The cutaneous resurfacing method in accordance with the present invention includes an ER:YAG laser light, whose radiation has an absorption depth of much less than that of $CO_2$ laser radiation, of the order of 50 micron. Despite the relatively low absorption depth, an appropriate peeling depth is reached by providing multiple pulses. The thickness of the layer of evaporated tissue may be controlled by the number of pulses, the delay between pulses and varying pulse parameters.

ER:YAG lasers produce radiation of 2.94 $\mu$m, with an energy per pulse of up to 1 J. Absorption depth of the radiation is typically about 10 $\mu$m. Thus, to evaporate an epidermis, a train of pulses should be used. Typical delay between the laser pulses should be in the range of 0.5–10 msec. The time should preferably be shorter than, or on the order of, the epidermis thermal relaxation time.

Thus, it should be apparent that there has been provided in accordance with the present invention a treatment device that includes a flashlamp or a near infrared pulsed laser in another embodiment, an ER:YAG laser and a coupler that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The embodiments of the invention in which an exclusive property or privilege is claimed are defined as follows:

1. A method of smoothing wrinkles in a region of wrinkled skin comprising the steps of:
    applying pulsed light to a surface of said region of wrinkled skin for heating said region of wrinkled skin;
    heating collagen in said region of wrinkled skin to a temperature that will shrink the collagen sufficiently to reduce the wrinkles,
    wherein said step of applying pulsed light includes a step of applying non-coherent light having wavelength in the range of 500–2000 nm.

2. The method of claim 1 wherein the step of applying pulsed light includes a step of applying light having fluence in the range of 5 to 200 $J/cm^2$.

3. The method of claim 1 wherein the step of applying pulsed light includes a step of applying light having pulse duration in the range of 1 to 300 milliseconds.

4. The method of claim 1 wherein the step of applying pulsed light includes a step of applying light pulses modulated from short pulses.

5. The method of claim 1 wherein the step of applying pulsed light includes a step of applying light having a spot size in the range of 1 mm to 10 cm.

6. The method of claim 1 further including a step of directing the light to the skin using a flexible light guide.

7. The method of claim 1 further including a step of directing the light to the skin using a rigid light guide.

8. The method of claim 1, further comprising a step of protecting the epidermis and outer layers of the skin by cooling the epidermis and outer layers of the skin.

9. The method of claim 8, further including a step of controlling a pulse duration and applying multiple pulses to control a temperature distribution within the skin.

* * * * *